United States Patent
Maroney et al.

(10) Patent No.: US 7,431,736 B2
(45) Date of Patent: Oct. 7, 2008

(54) DEVICE AND METHOD FOR POSITIONING AN ECCENTRIC HUMERAL HEAD OF A HUMERUS PROSTHESIS FOR A SHOULDER ARTHROPLASTY

(75) Inventors: Brian Maroney, Ft. Wayne, IN (US);
Michael Coon, Warsaw, IN (US);
Jeffrey Ondrla, Leesburg, IN (US);
Todd Durniak, Ft. Wayne, IN (US);
Joseph Iannotti, Bentleyville, OH (US);
Gerald Williams, Villanova, PA (US)

(73) Assignee: DePuy Products, Inc., Warsaw, IN (US)

( * ) Notice: Subject to any disclaimer, the term of this patent is extended or adjusted under 35 U.S.C. 154(b) by 629 days.

(21) Appl. No.: 10/844,208

(22) Filed: May 12, 2004

(65) Prior Publication Data
US 2004/0210317 A1    Oct. 21, 2004

Related U.S. Application Data

(63) Continuation of application No. 09/904,752, filed on Jul. 13, 2001, now abandoned.

(60) Provisional application No. 60/221,657, filed on Jul. 28, 2000.

(51) Int. Cl.
*A61F 2/30* (2006.01)
*A61F 2/40* (2006.01)

(52) U.S. Cl. ................. 623/18.11; 623/19.11

(58) Field of Classification Search .............. 623/18.11, 623/19.11–19.14, 22.4–22.47, 23.39, 23.4, 623/23.47, 22.11, 22.12; 606/89, 102
See application file for complete search history.

(56) References Cited

U.S. PATENT DOCUMENTS

| 4,795,469 A | 1/1989 | Oh |
| 5,314,479 A | 5/1994 | Rockwood, Jr. et al. |

(Continued)

FOREIGN PATENT DOCUMENTS

EP    0 612 509    8/1994

(Continued)

OTHER PUBLICATIONS

Marketing brochure entitled "Global Total Shoulder Arthroplasty System" of DePuy Orthopaedics, Inc., 1994.

*Primary Examiner*—Corrine McDermott
*Assistant Examiner*—Cheryl Miller
(74) *Attorney, Agent, or Firm*—Maginot, Moore & Beck

(57) ABSTRACT

A kit and associated method is for implanting a prosthetic device in a resected bone such as a humerus. The kit includes a trial assembly including a trial body portion having a trial bore defined therein, and a trial head portion having (i) a trail head member which includes a trial offset indicia, and (ii) an eccentrically located trial stem extending from the trial head member, the trial head stem being configured to be received within the trial bore. The kit also includes a final prosthesis assembly including a final body portion having a final bore defined therein, and a final head portion having (i) a final head member which includes a final offset indicia, and (ii) an eccentrically located final head stem extending from the final head portion, the final head stem being configured to be received within the final bore.

14 Claims, 10 Drawing Sheets

U.S. PATENT DOCUMENTS

| | | |
|---|---|---|
| 5,358,526 A | 10/1994 | Tornier |
| 5,645,607 A | 7/1997 | Hickey |
| 5,702,447 A | 12/1997 | Walch et al. |
| 5,702,457 A | 12/1997 | Walch et al. |
| 5,885,297 A | 3/1999 | Matsen, III |
| 5,910,171 A | 6/1999 | Kummer et al. |
| 6,102,953 A | 8/2000 | Huebner |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,368,353 B1 | 4/2002 | Arcand |
| 6,508,840 B1 * | 1/2003 | Rockwood et al. ........ 623/19.12 |
| 6,589,282 B2 * | 7/2003 | Pearl ........................ 623/19.14 |
| 2001/0053935 A1 | 12/2001 | Hartdegen et al. |
| 2002/0156534 A1 | 10/2002 | Grusin et al. |
| 2003/0028253 A1 | 2/2003 | Stone et al. |

FOREIGN PATENT DOCUMENTS

| | | |
|---|---|---|
| EP | 0 931 522 | 1/1998 |
| FR | 2 743 492 | 7/1997 |

* cited by examiner

DEVICE AND METHOD FOR POSITIONING AN ECCENTRIC HUMERAL HEAD OF A HUMERUS PROSTHESIS FOR A SHOULDER ARTHROPLASTY

This application is a continuation of application Ser. No. 09/904,752, filed on Jul. 13, 2001 now abandoned that, in turn, claims the benefit of U.S. Provisional Application Ser. No. 60/221,657 that was filed Jul. 28, 2000.

FIELD OF THE INVENTION

The present invention relates to prostheses for reconstructive surgery of a gleno-humeral joint and, more particularly, to the positioning of an eccentric head of a humerus prostheses for reconstructive surgery of a gleno-humeral joint.

BACKGROUND

In total shoulder arthroplasty, reproduction of the correct location of the humeral articular surface is critical to reestablishing joint biometrics. Translating this location to the implant is thus of critical importance.

Each shoulder arthroplasty needs to be adapted to the patient's unique combination of soft tissue and bone anatomy. As well, the patient typically has high expectations of the function and durability of the arthroplasty. Thus, the implant and the implant technique must be precise.

In view of this, there has been developed a range of prostheses designed to fit the various sizes and shapes of people's anatomy. For shoulder arthroplasty, a prosthesis with a humerus head has been developed. It has been recognized, though, that the humerus head may need to be eccentrically mounted relative to the prosthesis body in order to cover the exposed, resected humerus head. There has been a problem, however, with the ability to adequately position the eccentric head on the implant in order to meet the needs of every patient. Typically, the eccentric head is positionable in only a few select orientations relative to the eccentricity.

Thus, there is a need for an prosthetic implant that can utilize an eccentric head wherein the eccentric head may be positioned in any number of rotatably eccentric positions.

SUMMARY OF THE INVENTION

The present invention is a method, apparatus and corresponding implant for positioning an eccentric head on a trail implant/broach and transferring or translating the eccentric position of the head onto the actual or definitive implant. The present invention allows the eccentric head to be positioned in an infinite amount of positions or orientations to best reproduce the articular geometry of the patient. The infinite dialability is optimum for reconstruction purposes.

Because each shoulder arthroplasty needs to be adapted to the patient's unique combination of soft tissue and bone anatomy, the present system maximizes the surgeon's flexibility in matching a wide variety of anatomic requirements. The present invention places a premium on secure fixation, conservation of bone and optimization of mechanics.

During the trialing process, the humeral head trial is lockable into one of an infinite variety of rotational positions (a set orientation) that then may be transferred to the definitive humeral head of the definitive implant. A means is provided for locking the eccentric trial head to the trial/broach in a set orientation that allows for the trialing process to occur without spinning of the eccentric trial head in the broach taper. In one form, this is accomplished via a captured screw in the eccentric trial head that extends beyond the taper of a neck of the eccentric trial head. The captured screw engages threads in a bottom of a bore in a taper in the broach.

Once the eccentric head has been threaded onto the trial broach, it is rotated into a correct position covering the resected humeral head surface. The eccentric head may be rotated into an infinite number of positions on the trail broach without having to be locked in any particular orientation. Once the eccentric head is in position, the captured screw is tightened or locked. Trial reduction is carried out and if deemed satisfactory, the broach/eccentric head trail head assembly (or trial assembly) is removed as a one piece unit from the humerus of the patient.

In accordance with an aspect of the present invention, the eccentric head includes a mark or indicia showing the position of maximum offset. Once the trial assembly has been removed, from the patient's humerus, it is placed in an impaction stand or block. The impaction stand allows the measurement of the orientation of the eccentric head (by the indicia) on the trial broach, and the translation or transference of that orientation onto the definitive implant. The impaction stand has a scale or demarcations on a surface thereof. The orientation of the indicia of the eccentric head is noted relative to the scale.

The trial assembly is then removed from the impaction stand and the appropriate size of the definitive implant is placed in the impaction stand. An appropriate size of definitive eccentric head is placed on the definitive implant. The definitive eccentric head includes an indicia either as an etched or otherwise arrow or other marking on the nonarticulating surface (or by a removable sticker or the like on the articulating surface) showing the position of maximum offset (in like manner to the trial eccentric head). The indicia of the definitive eccentric head is orientated or aligned with the scale to the same number or marking as the trial eccentric head.

Once the definitive eccentric head has been properly aligned, the definitive eccentric humeral head is impacted into place onto the definitive implant while on the impaction stand. In this manner, the appropriate position of the humeral head for the definitive implant has been successfully transferred from the trial assembly.

It can be appreciated from the foregoing, that the eccentric head may be rotationally positioned in an infinite number of positions, both during trialing and during the final implant.

In accordance with one embodiment of the present invention, there is provided a method of implanting a final prosthesis assembly in a resected bone. The method includes the step of positioning a trial assembly in the resected bone, the trial assembly including a trial body portion having a trial bore defined therein, and a trial head portion having (i) a trial head member which includes a trial offset indicia, and (ii) an eccentrically located trial head stem extending from the trial head member, the trial head stem being configured to be received within the trial bore. The method further includes the step of rotating the trial head portion relative to the trial body portion while the trial assembly is positioned in the resected bone so as to position the trial head portion relative to the trial body portion at an aligned orientation whereby the trial head portion covers a resected surface of the resected bone. In addition, the method includes the step of removing the trial assembly from the resected bone after the rotating step. The method also includes the step of positioning the trial assembly in a scale mechanism whereby the trial offset indicia of the trial head portion aligns with a value on the scale mechanism. Moreover, the method includes the step of securing a final head portion to a final body portion based on the value so as to form the final prosthesis assembly. Additionally, the method includes the step of implanting the final prosthesis assembly in the resected bone after the securing step.

Pursuant to another embodiment of the present invention, there is provided a method of implanting a final prosthesis assembly in a resected bone. The method includes the step of providing a trail assembly which includes a trial body portion having a trial bore defined therein, and a trial head portion having (i) a trial head member which includes a trial offset indicia, and (ii) an eccentrically located trial head stem extending from the trial head member. The method further includes the step of positioning the trial body portion in the resected bone. Also, the method includes the step of positioning the trial stem in the trial bore after the trial body positioning step. In addition, the method includes the step of moving the trial head portion in relation to the trial body portion after the trial stem positioning step so as to locate the trial head portion relative to the trial body portion at a user-selected orientation. The method also includes the step of securing the trial head portion to the trial body portion at the user-selected orientation. Additionally, the method includes the step of removing the trial assembly from the resected bone after the securing step. Furthermore, the method includes the step of positioning the trial assembly in a scale mechanism after the removing step whereby the trial offset indicia of the trial head portion aligns with a value on the scale mechanism. Moreover, the method includes the step of attaching a final head portion in fixed relation to a final body portion based on the value so as to form the final prosthesis assembly. The method also includes the step of implanting the final prosthesis assembly in the resected bone after the attaching step.

According to still another embodiment of the present invention, there is provided a kit used during the implantation of a prosthesis. The kit includes a trial assembly including a trial body portion having a trial bore defined therein, and a trial head portion having (i) a trail head member which includes a trial offset indicia, and (ii) an eccentrically located trial stem extending from the trial head member, the trial head stem being configured to be received within the trial bore. The kit also includes a final prosthesis assembly including a final body portion having a final bore defined therein, and a final head portion having (i) a final head member which includes a final offset indicia, and (ii) an eccentrically located final head stem extending from the final head portion, the final head stem being configured to be received within the final bore.

According to yet another embodiment of the present invention, there is provided a kit which includes a trial assembly including (i) a trial body portion, (ii) a trial head portion which includes a trial offset indicia, and (iii) a fastener for securing the trial head portion to the trial body portion. The kit further includes a final prosthesis assembly including a final body portion having a final bore defined therein, and a final head portion having (i) a final head member which includes a final offset indicia, and (ii) an eccentrically located final head stem extending from the final head portion, the final head stem being configured to be received within the final bore.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views.

DETAILED DESCRIPTION

Figures 1A, 1B:
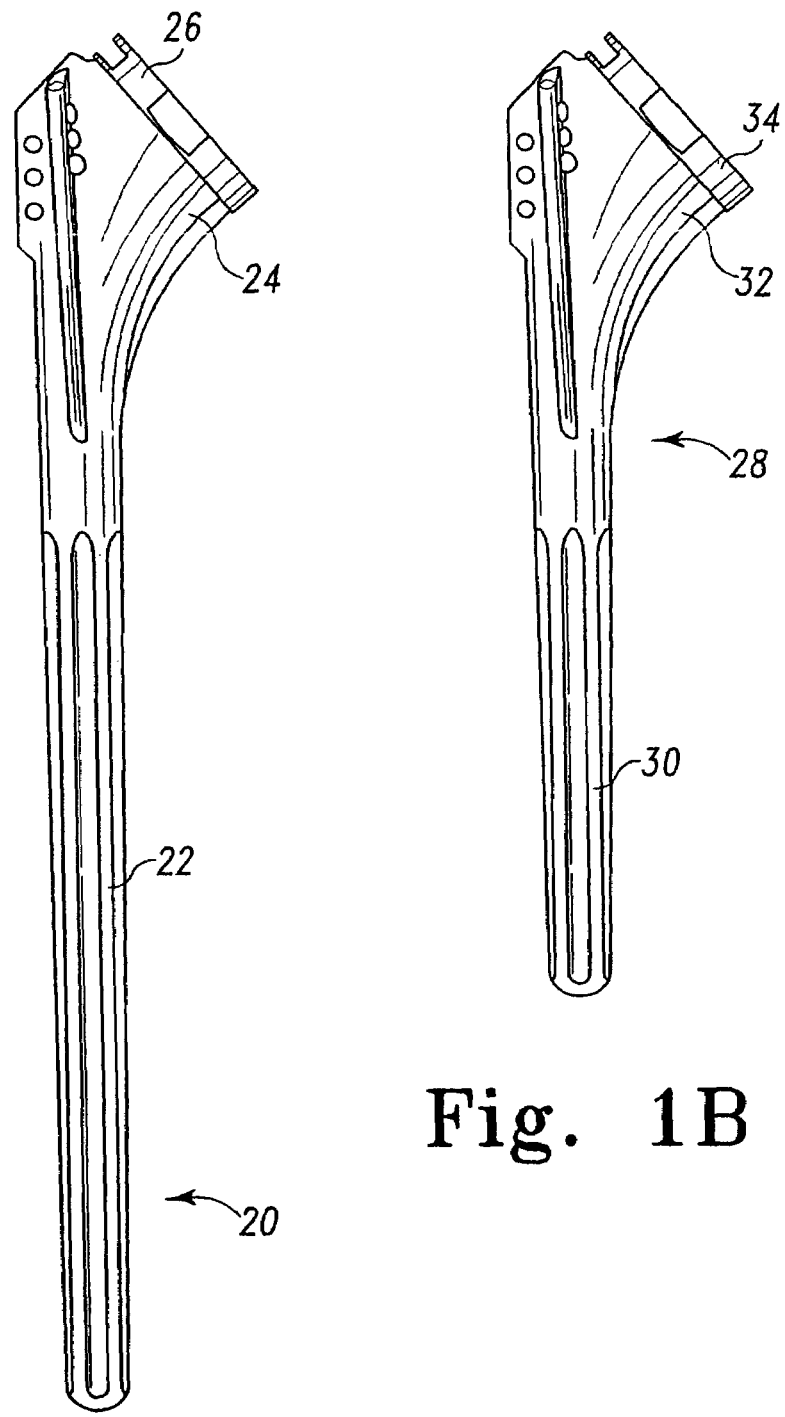
FIGS. 1A and 1B are elevational views of exemplary humerus prostheses/trail broach bodies used in conjunction with the eccentric head of the present invention.

With reference to FIG. 1A, there is shown an exemplary, 210 mm humerus prosthesis or trial broach generally designated 20. The humerus prostheses/trial broach 20 includes a stem 22 extending from a neck 24. The neck 24 terminates in a generally flat surface 26 that is adapted to be seated on a surface of a resected humerus head of a patient's humerus. In FIG. 1B, there is shown an exemplary, 138 mm humerus prosthesis or trial broach generally designated 28. The humerus prostheses/trial broach 28 includes a stem 30 extending from a neck 32. The neck 32 terminates in a generally flat surface 34 that is adapted to be seated on a surface of a resected humerus head of a patient's humerus.

Figure 2:
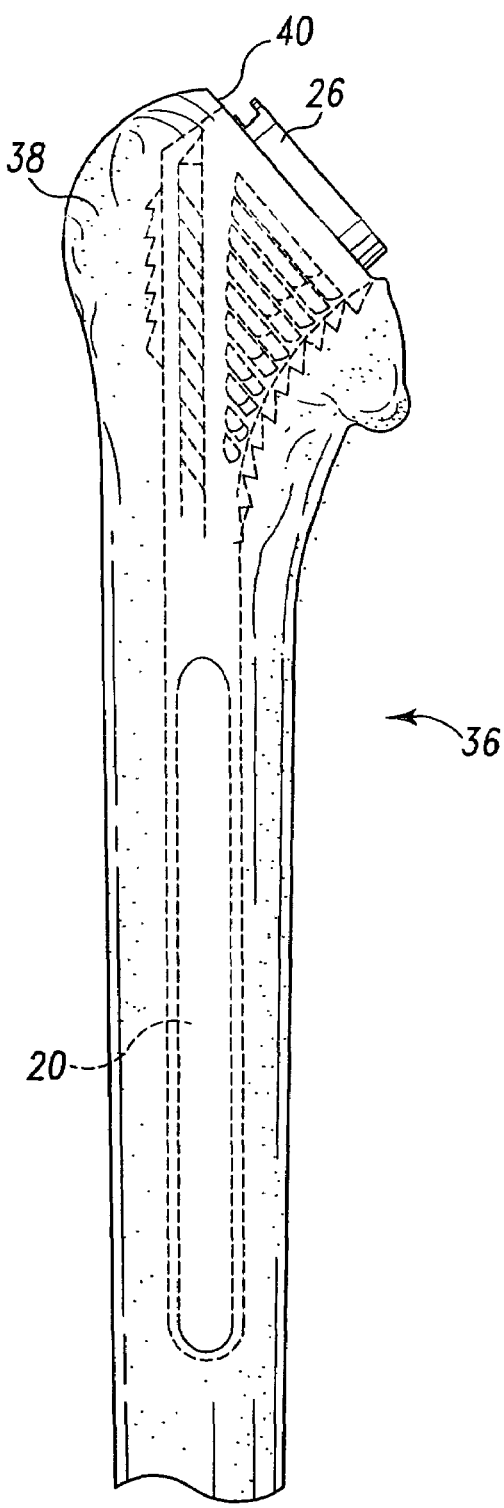
FIG. 2 is an enlarged, side sectional view of a partial humerus with a portion of the humerus head resected (removed) and a trail broach inserted into the humerus.

In FIG. 2, there is shown a patient's humerus 36 wherein the humerus head 38 has been resected in accordance with standard shoulder arthroplasty surgery. It is beyond the scope of the present invention to discuss humerus head resection. Various texts and papers may be consulted for this procedure.

After the humerus head 38 has been resected, the humerus head must be sized for a prosthetic head of the implant. Various sizes are available such as 44, 48 and 52 mm. It will be assumed that an eccentric head will be chosen. In FIG. 2, the medullary canal of the humerus 36 has been reamed and the trial broach 20 has been placed thereon. The flat 26 is in contact with a surface 40 of the resected humerus head 38. The trial broach 20 is ready to be fitted with a trial eccentric head.

Preoperative evaluation of the Humerus 36 with templates (not shown) helps determine the size of the prostheses and level of humerus head resection. Humeral head resection is accomplished as is known in the art or with other methods the detail of which is beyond the scope of the present invention and this disclosure.

Figure 7:
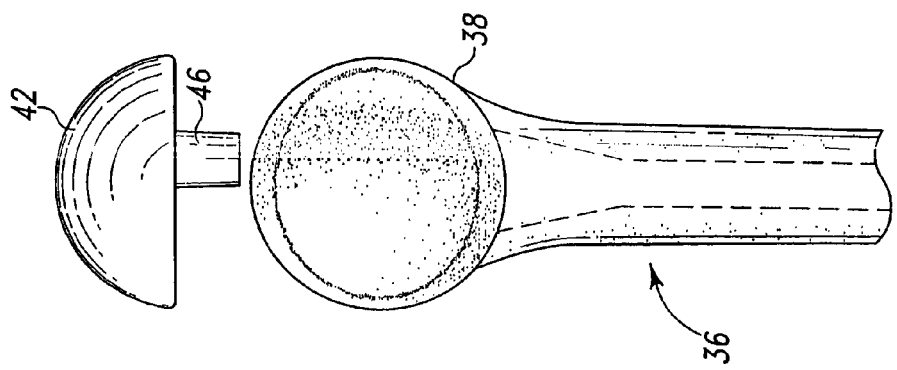
FIG. 7 is a front elevational view of the partial humerus of FIG. 5 showing the trial eccentric humerus head covering the surface of the resected humerus head.
Figure 6:
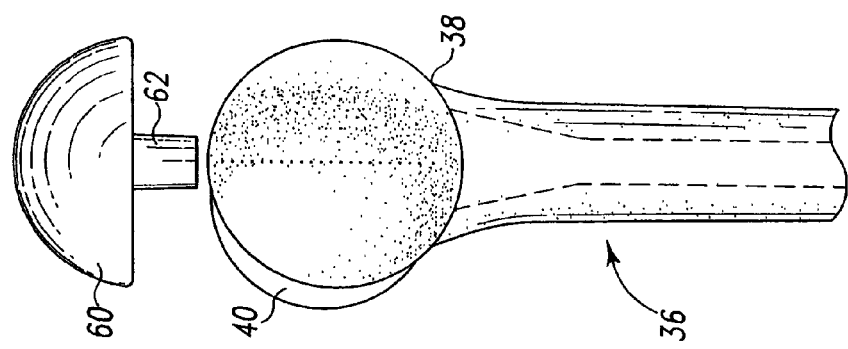
FIG. 6 is a front elevational view of the partial humerus of FIG. 5 showing a trial standard humerus head that exposes a portion of the surface of the resected humerus head.
Figure 5:
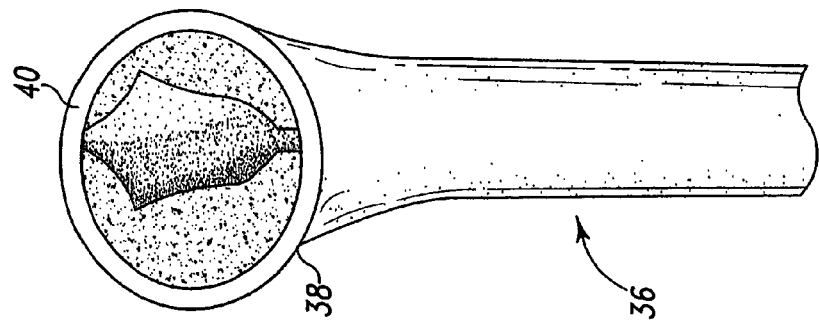
FIG. 5 is a front elevational view of a partial humerus with the humerus head resected.

Briefly, in FIGS. 5-7 there is shown a reason for selecting an eccentric head. FIG. 5 shows the humerus 36 whose humerus head 38 has been resected. It is now necessary to find a trial head that will cover the humerus surface 40 formed by the resection. In FIG. 6 a trail standard head 60 having a tapered stem 62 is shown in position over the surface 40. It can be seen that the surface 40 is visible around the periphery of the trial standard head 60. A centerline shows how the trial standard head 60 fits over the surface 40. Even with rotation of the trial standard head 60, the surface 40 is exposed. Thus, the trial standard head 60 is not appropriate. In FIG. 7, a trial eccentric head 42 having a tapered stem 46 is shown in position over the surface 40. It can be seen that with the correct rotation/orientation/placement of the trial eccentric head 42, the entire surface 40 is covered. With an infinite number of rotational positions, an eccentric head is thus appropriate.

Figure 4:
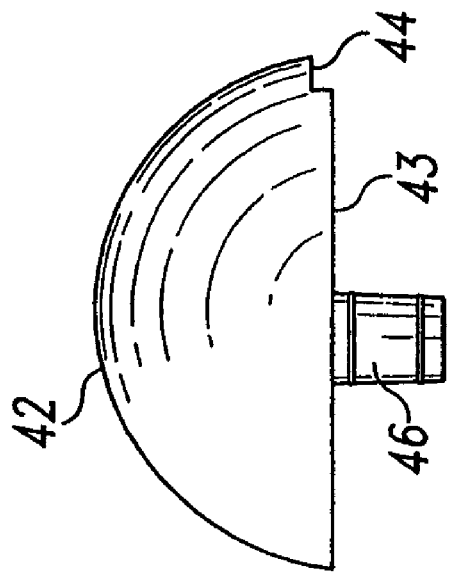
FIG. 4 is a side elevational view of the eccentric trial humerus head of FIG. 3.
Figure 3:
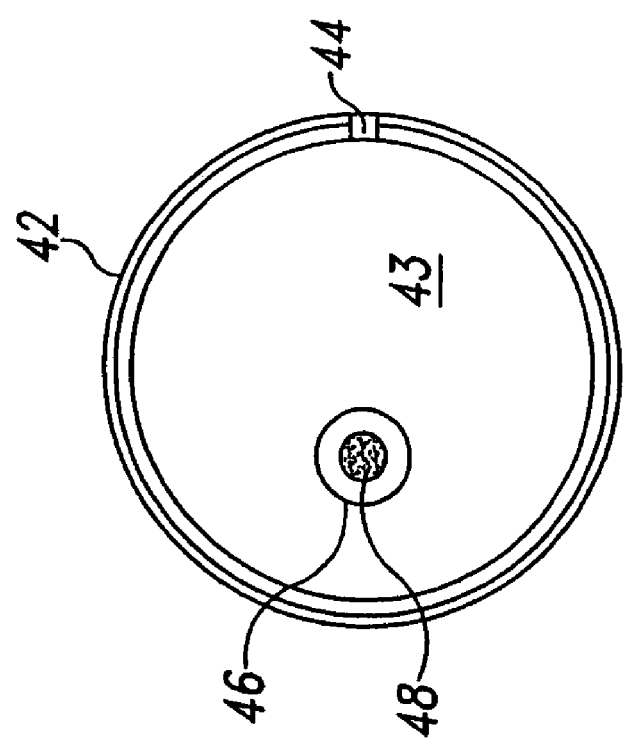
FIG. 3 is a bottom plan view of an eccentric trail humerus head.

Referring to FIGS. 3, and 4, a trial eccentric head 42 in accordance with the principles of the present invention is shown. Four eccentric head 42 sizes may be provided, 44 mm, 48 mm, 52 mm, and 56 mm. The trial eccentric head 42 includes a tapered stem 46 that is positioned off center (approximately a 4 mm offset) such that an eccentricity during rotation thereabout is defined or formed. The stem 46 extends essentially perpendicularly from a bottom surface 43 of the trial eccentric head 42 and includes a bore 48 that extends through the stem 46 and the head 42. The trial eccentric head 42 includes an indicia (here a notch) 44 that indicates a maximum offset position for the eccentric head 42. It should be appreciated that other types of indicia may be used. Here the notch 44 is located on the edge of the articular surface of the eccentric head 42.

Figure 8:
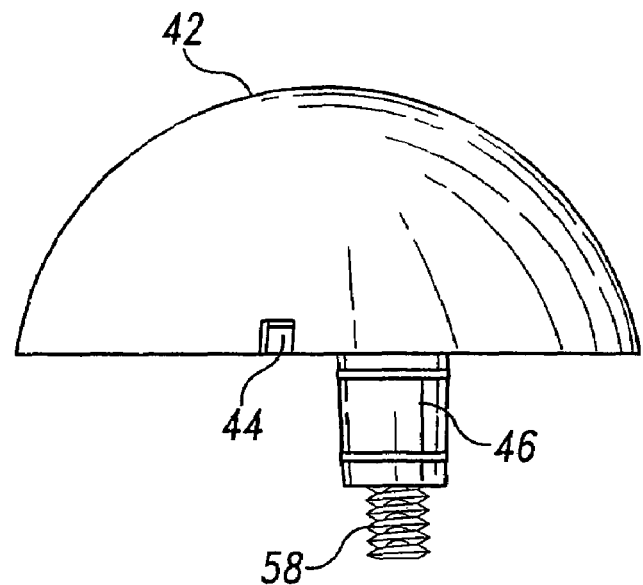
FIG. 8 is an enlarged side elevational view of the trial eccentric humerus head of FIGS. 3 and 4 having a seating screw extending therefrom.
Figure 9:
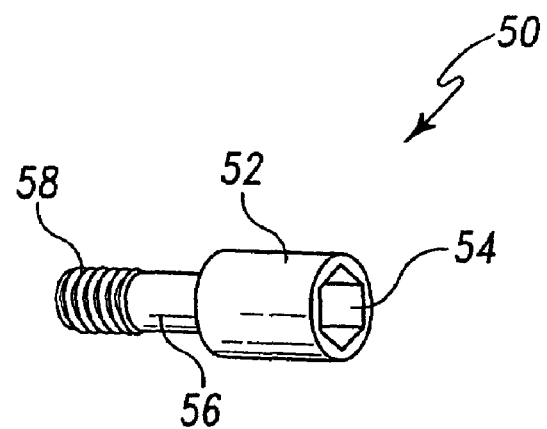
FIG. 9 is an enlarged perspective view of the seating screw of FIG. 8.

Referring to FIG. 9, a retaining screw or the like 50 for the trial assembly (trial eccentric head and trial broach) is shown. The retaining screw 50 includes a head 52 having an opening 54 for receiving a screw driver or the like. The opening may be hex shape or otherwise. Extending from the head 52 is a shank 56 terminating in threads 58. The retaining screw 50 is designed to fit into the bore 48 of the trial eccentric head 42 with its threads 58 extending therefrom (see FIG. 8).

Figure 11:
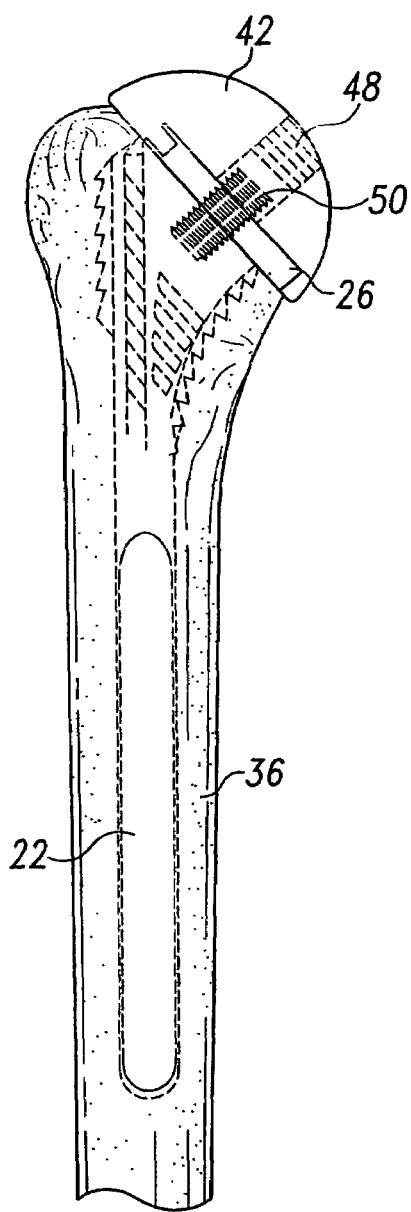
FIG. 11 is an enlarged, side sectional view of a partial humerus with the trail assembly (broach and eccentric head inserted into the humerus.
Figure 10:
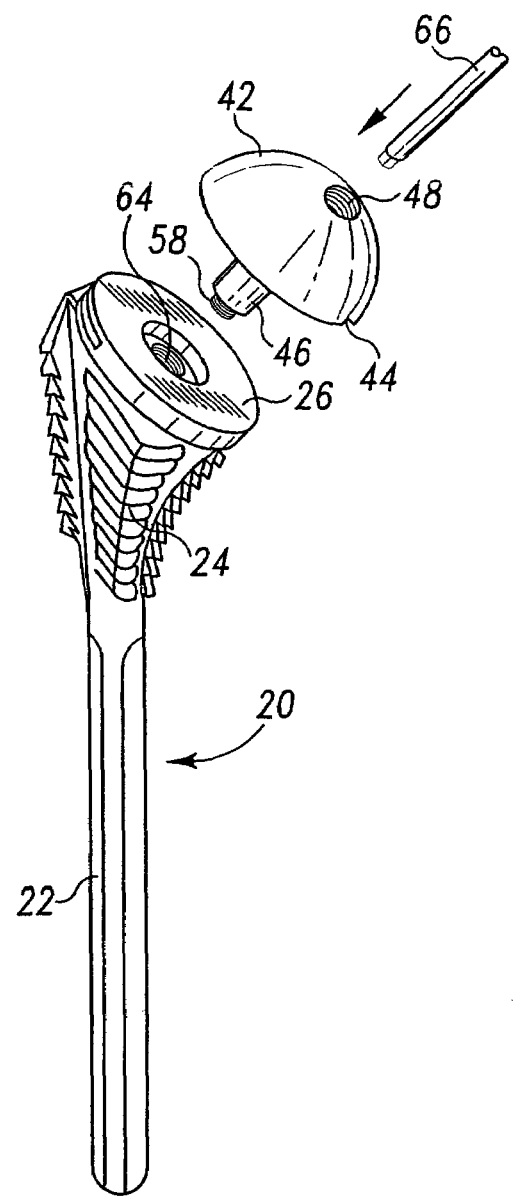
FIG. 10 is a perspective view of a trial eccentric head being attached to the trial broach via a driver.
Figure 12:
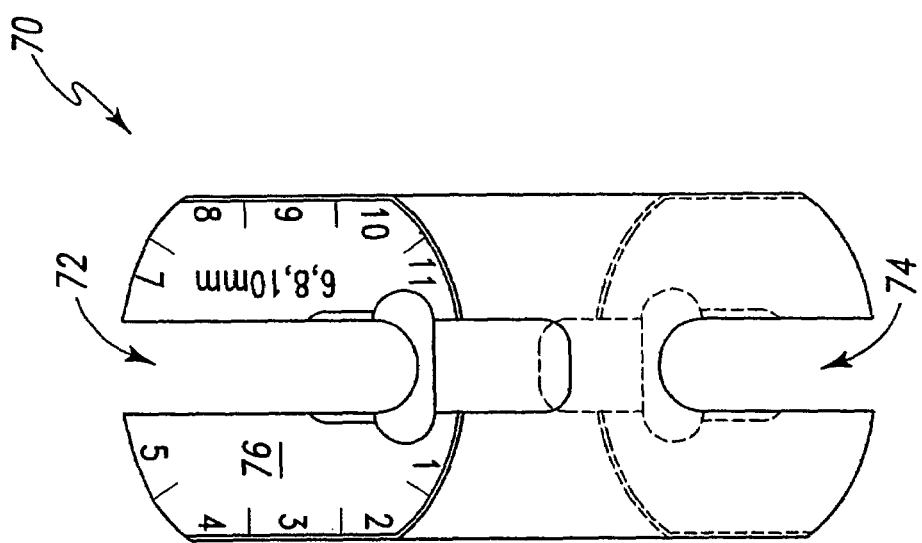
FIG. 12 is a top perspective view of an impaction stand.
Figure 13:
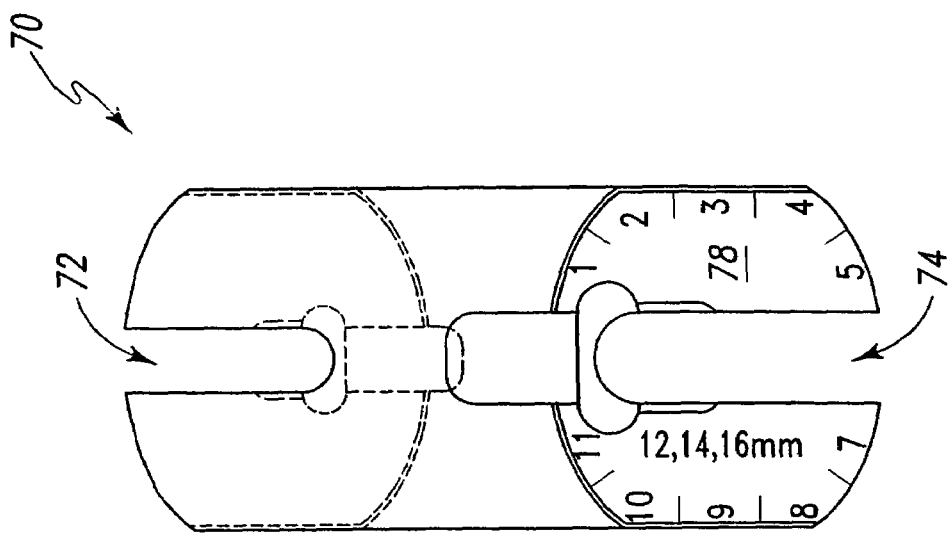
FIG. 13 is a bottom perspective view of the impaction stand of FIG. 12.
Figure 14:
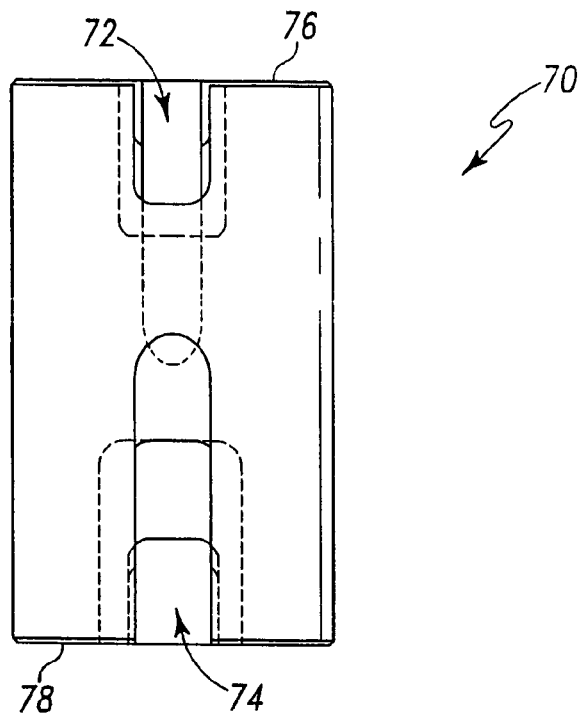
FIG. 14 is a side elevational view of the impaction stand of FIGS. 12 and 13.
Figures 15, 16:
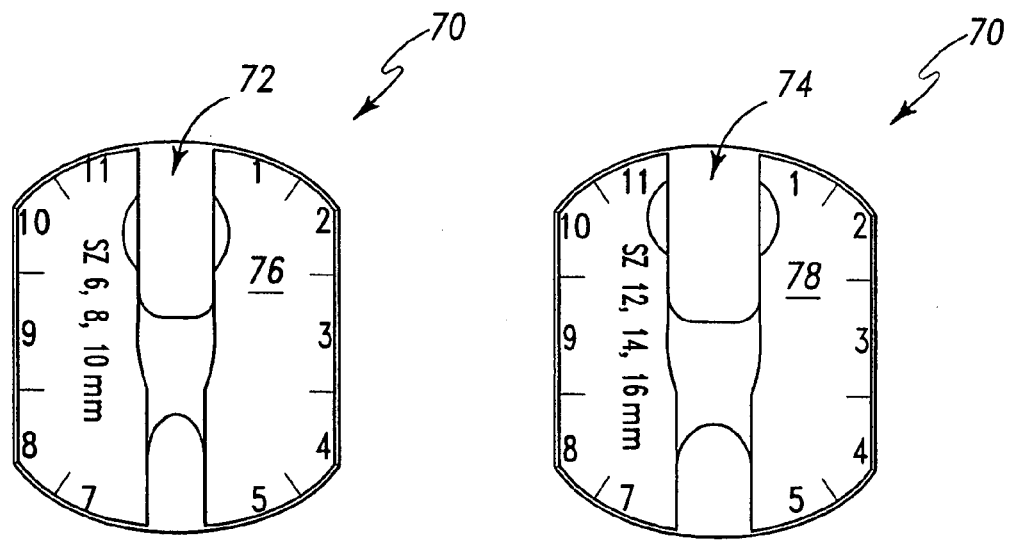
FIG. 15 is a top plan view of the impaction stand of FIGS. 12-14.
FIG. 16 is a bottom plan view of the impaction stand of FIGS. 12-14.

Referring to FIG. 10, the trial broach 20 is shown wherein the trial eccentric head 42 is ready to be attached thereto. Using an appropriate screw driver 66, the eccentric trial head 42 is attached to the trial broach by threading the screw 50 into a complementary threaded bore 64 in the flat 26. Once the eccentric head 42 is attached to the trial broach 20 it is inserted into the humerus 36 (see FIG. 11). Once the trial prosthesis is in place as depicted in FIG. 11, the screw 50 may be loosened to rotate the eccentric head 42 to a proper orientation. Once a proper rotational orientation has been achieved, the screw 50 is tightened. The trial prosthesis may now be removed from the humerus 36. Once the trial prosthesis has been removed from the humerus 36 it is ready to be place in an impaction stand or block in accordance with the principles of the present invention. The position of the eccentric head 42 is now ready to be transferred or reproduced in the final or definitive prosthetic implant that will remain in the patient.

Referring to FIGS. 12-16, there is shown an impaction stand or block generally designated 70 in accordance with the principles of the present invention. The impaction stand 70 may be made of a suitable plastic or the like and is essentially a hexagonal cylinder. The impaction stand 70 is designed to accommodate various sizes of trail broaches/final prostheses. To this end, the impaction stand 70 has two faces or surfaces 76 and 78 on opposite sides thereof. Extending diagonally from the surface 76 to an outside surface of the cylinder is a first channel 72. Extending diagonally from the surface 78, opposite in orientation to the first channel 72, is a second channel 74. The second channel 74 extends to an outside surface of the cylinder. The first and second channels 72 and 74 and their respective surfaces 76 and 78, are designed to accommodate various sizes of trial broaches/final prostheses. In the figures, surface 76/channel 72 is designed to hold trial broaches/final prostheses of sizes 6 mm, 8, and 10 mm, while the surface 78/channel 74 is designed to hold trial broaches/final prostheses of sizes 12 mm, 14 mm, and 16 mm. Of course, it should be appreciated that the impaction block 70 may be designed for other sizes, or several blocks for the various sizes.

Each surface 76 and 78 includes an indicia or scale in the manner of a clock or the like that divides the periphery thereof into sections. The scale is used to reference the position of the notch 44 of the trial eccentric head 42 when the trial assembly is place in the impaction stand (as well as the final assembly as indicated below).

Figure 17:
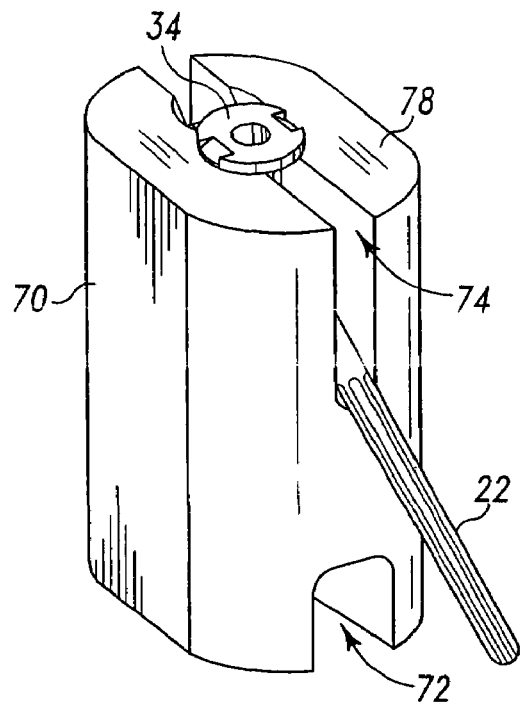
FIG. 17 is a perspective view of the impaction stand with a broach or implant seated thereon.
Figure 18:
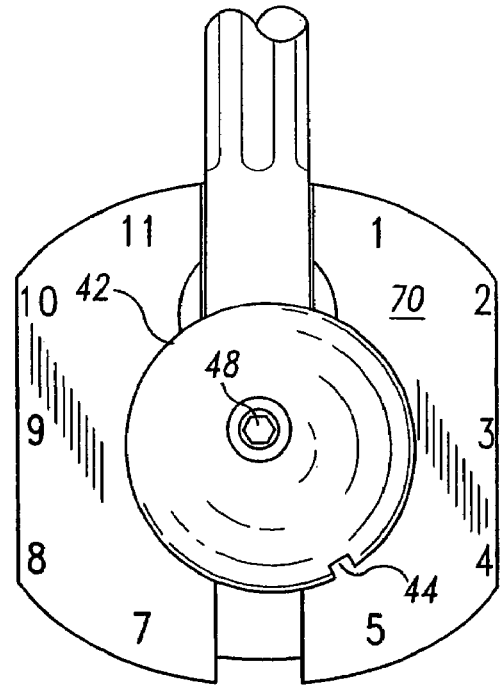
FIG. 18 is an enlarged top plan view of a trial assembly seated on the impaction stand with the indicia (notch) of the trial eccentric head positioned at "5"

Referring to FIGS. 17 and 18 the trial assembly is placed into the impaction stand 70 (in FIG. 17, the eccentric head is not present to illustrate how the stem 22 fits in the impaction stand 70/channel 74). As seen in FIG. 18 the position of the notch 44 in the trial eccentric head 42 is noted (here at position 5) for transference or reproduction onto the final prosthesis.

Figure 19:
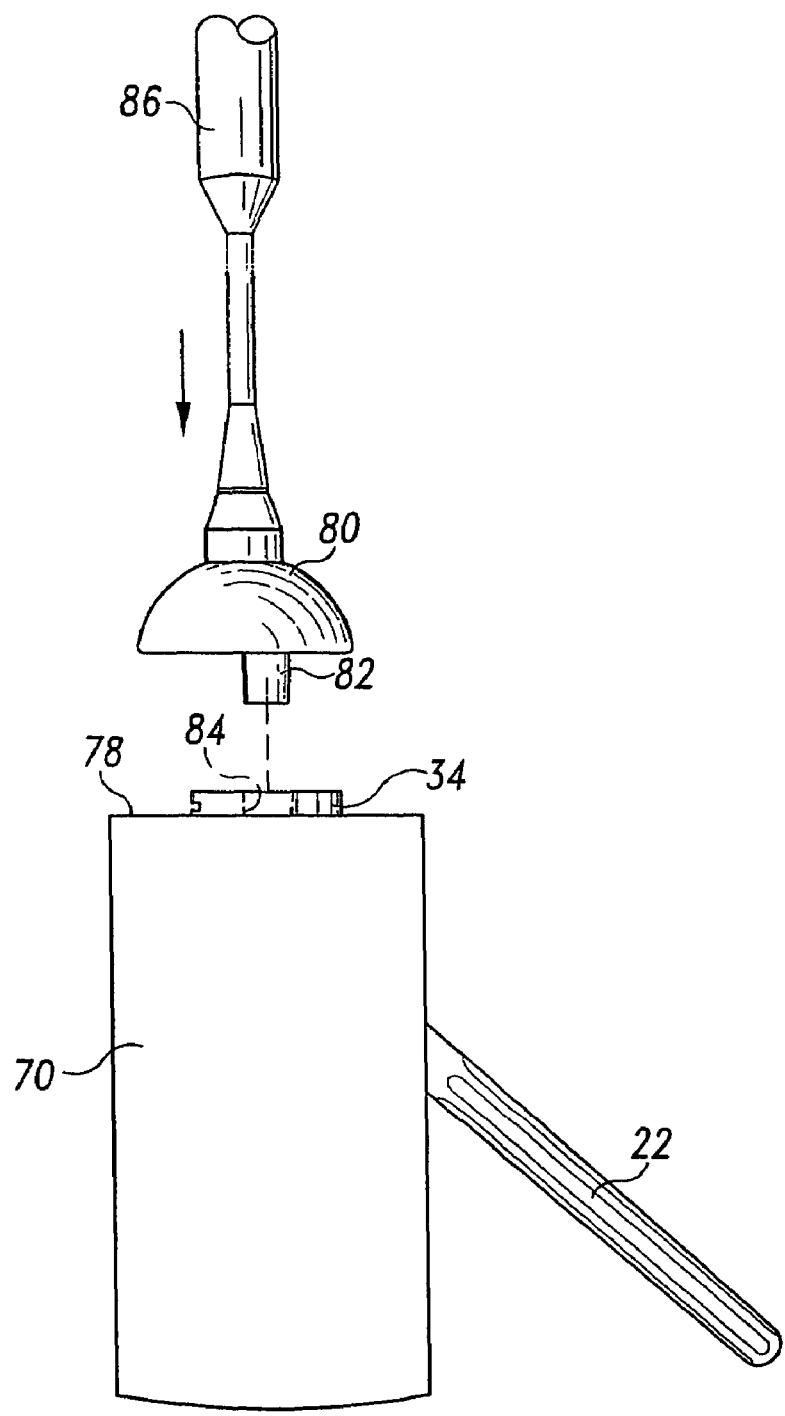
FIG. 19 is a perspective view of the impaction stand with a definitive implant seated thereon with a definitive eccentric humerus head ready to be impacted onto the implant.

The final step is to fit the final eccentric head onto the final humeral stem (of the same size as the trial broach). The trial assembly is removed from the impaction stand 70 and the final humeral stem/body is placed therein (see FIG. 17). In FIG. 19, a final eccentric head 80 is chosen of the same size as the trial eccentric head 42. The final eccentric head 80 is held by an impactor 86 such as a Delrin-tipped impactor. The final eccentric head includes an indicia, either as a permanent mark or the like on the nonarticulating surface thereof or as a removable sticker or the like on the articulating surface thereof, that indicates the maximum offset in like manner to the trial eccentric head 42. The indicia of the final eccentric head 80 is aligned with the marking or indicia on the scale of the surface 78 that is the same as that noted above (here "5"). The taper 82 of the eccentric head 80 is inserted into a complementary tapered bore 84. Keeping the indicia of the eccentric head 80 as noted, the final eccentric head 80 is impacted onto the final humeral stem with a mallet (not shown) onto the impactor 86. The final assembly is now ready to be inserted back into the patient's humerus.

While this invention has been described as having a preferred design and/or configuration, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains. For example, while the invention is discussed in the context of implanting a prosthesis in the humerus, the present is application to implantation of a prosthesis into any bone which forms a joint such as the shoulder, hip, etc. For instance, the present in invention is application to the implantation of a prosthesis into a femur.

What is claimed is:

1. A prosthesis implantation method. comprising the steps of:
    (a) positioning a trial assembly in a resected bone, said trial assembly including a trial body portion having a trial bore defined therein, and a trial head portion having (i) a trial head member which includes a trial offset indicia, and (ii) an eccentrically located trial head stem extending from said trial head member, said trial head stem being configured to be received within said trial bore;
    (b) rotating said trial head portion relative to said trial body portion while said trial assembly is positioned in said resected bone so as to position said trial head portion relative to said trial body portion at an aligned orientation in which said trial head portion covers a resected surface of said resected bone;
    (c) removing said trial assembly from said resected bone after step (b);
    (d) positioning said trial assembly in a scale mechanism having a plurality of distinct values displayed thereon after step (c), said trial offset indicia of said trial head portion being aligned with one of said plurality of distinct values displayed on said scale mechanism in response to step (d);
    (e) securing a final head portion to a final body portion based on said one of said plurality of distinct values after step (d) so as to form a final prosthesis assembly; and
    (f) implanting said final prosthesis assembly in said resected bone after step (e),
    wherein said scale mechanism includes an indicia surface, and
    wherein said plurality of distinct values are displayed on said indicia surface, and
    wherein said scale mechanism includes a channel defined therein, and step (d) includes the step of locating said trial body portion within said channel.

2. The method of claim 1, further comprising the step of securing said trial head portion to said trial body portion when said trial head portion is positioned relative to said trial body portion at said aligned orientation.

3. The method of claim 2, wherein:
    said trial body portion includes a set of internal threads located within said trial bore,
    said trial head portion further includes an externally threaded fastener positioned within a passageway which extends through said trial head portion, and
    said securing step includes the step of advancing said externally threaded fastener into meshing engagement with said set of internal threads so as to secure said trial head portion in fixed relation to said trial body portion.

4. The method of claim 1, wherein:
    said trial body includes (i) a trial body stem, (ii) a neck attached to said trial body stem, and (iii) a flat attached to said neck, and
    said trial bore extends through said flat and into said neck.

5. The method of claim 1, wherein:
    said indicia surface is divided into a plurality of sections, and
    said one of said plurality of distinct values is identified on one of said plurality of sections.

6. The method of claim 1, wherein:
    said trial body portion locating step includes the step of locating said trial head portion adjacent to said indicia surface.

7. The method of claim 1, wherein said final head portion includes (i) a final head member having a final offset indicia, and (ii) an eccentrically located final head stem extending from said final head member.

8. The method of claim 7, wherein:
    said final head stem possesses a male taper configuration,
    said final body portion has a final bore defined therein,
    said final bore possesses a female taper configuration, and
    said securing step includes the step of advancing said final head stem into said final bore in a friction fit manner.

9. The method of claim 1, wherein said resected bone is a resected humerus.

10. A prosthesis implantation method, comprising the steps of:
    (a) positioning a trial assembly in a resected bone, said trial assembly including a trial body portion having a trial bore defined therein, and a trial head portion having (i) a trial head member which includes a trial offset indicia. and (ii) an eccentrically located trial head stem extending from said trial head member, said trial head stem being configured to be received within said trial bore;
    (b) rotating said trial head portion relative to said trial body portion while said trial assembly is positioned in said resected bone so as to position said trial head portion relative to said trial body portion at an aligned orientation in which said trial head portion covers a resected surface of said resected bone;
    (c) removing said trial assembly from said resected bone after step (b);
    (d) positioning said trial assembly in a scale mechanism having a plurality of distinct values displayed thereon after step (c), said trial offset indicia of said trial head portion being aligned with one of said plurality of distinct values displayed on said scale mechanism in response to step (d);
    (e) securing a final head portion to a final body portion based on said one of said plurality of distinct values after step (d) so as to form a final prosthesis assembly; and
    (f) implanting said final prosthesis assembly in said resected bone after step (e),
    wherein said final head portion includes (i) a final head member having a final offset indicia, and (ii) an eccentrically located final head stem extending from said final head member,
    wherein said scale mechanism includes an indicia surface,
    wherein said one of said plurality of distinct values is indicated on said indicia surface,
    wherein said scale mechanism further includes a channel defined therein, and
    wherein said securing step includes locating said final body portion within said channel.

11. The method of claim 10, wherein said securing step further includes locating said final head portion adjacent to said indicia surface.

12. The method of claim 11, wherein said securing step further includes positioning said final head portion relative to said final body portion at said aligned orientation.

13. The method of claim 12, wherein said step of positioning said final head portion relative to said final body portion includes the step of aligning said final offset indicia with said one of said plurality of distinct values identified on said indicia surface.

14. A prosthesis implantation method, comprising the steps of;
  (a) positioning a trial assembly in a resected bone, said trial assembly including a trial body portion having a trial bore defined therein, and a trial head portion having (i) a trial head member which includes a trial offset indicia. and (ii) an eccentrically located trial head stem extending from said trial head member. said trial head stem being configured to be received within said trial bore;
  (b) rotating said trial head portion relative to said trial body portion while said trial assembly is positioned in said resected bone so as to position said trial head portion relative to said trial body portion at an aligned orientation in which said trial head portion covers a resected surface of said resected bone:
  (c) removing said trial assembly from said resected bone after step (b);
  (d) positioning said trial assembly in a scale mechanism having a plurality of distinct values displayed thereon after step (c). said trial offset indicia of said trial head portion being aligned with one of said plurality of distinct values displayed on said scale mechanism in response to step (d);
  (e) securing a final head portion to a final body Dortion based on said one of said plurality of distinct values after step (d) so as to form a final prosthesis assembly; and
  (f) implanting said final prosthesis assembly in said resected bone after step (e),
  wherein said final head portion includes (i) a final head member having a final offset indicia, and (ii) an eccentrically located final head stem extending from said final head member,
  wherein said trial offset indicia includes a notch defined in a surface of said trial head member, and
  wherein said final offset indicia includes a removable sticker positioned on said final head member.

* * * * *